United States Patent [19]
Boiteux et al.

[11] Patent Number: 5,108,661
[45] Date of Patent: Apr. 28, 1992

[54] PROCESS FOR THE PREPARATION OF PURIFIED FATTY ALKYLDIETHANOLAMIDES PRODUCTS OBTAINED ACCORDING TO SAID PROCESS AND THEIR USE

[75] Inventors: Jean-Pierre Boiteux, Saix; Bernard Brancq, Le Chesnay; Nelly Lecocu, Castres; Frédéric Loussayre, Saix, all of France

[73] Assignee: Societe D'Exploitation De Produits Pour Les Industries Chimiques S.E.P.O.I.C., Paris, France

[21] Appl. No.: 467,565

[22] Filed: Jan. 19, 1990

[30] Foreign Application Priority Data

Jan. 31, 1989 [FR] France .................................. 8901219

[51] Int. Cl.$^5$ .............................................. C09F 7/00
[52] U.S. Cl. ..................................... 252/357; 554/66; 252/548
[58] Field of Search .......................................... 260/404

[56] References Cited

FOREIGN PATENT DOCUMENTS 0253046 2/1970 U.S.S.R. ............................... 260/404

Primary Examiner—Jose G. Dees
Assistant Examiner—Deborah D. Carr
Attorney, Agent, or Firm—Dennison, Meserole, Pollack & Scheiner

[57] ABSTRACT

The present invention relates to a process for the preparation of fatty diethanolamides with low diethanolamine content, characterized in that the raw product obtained by conventional reaction between the diethanolamine and said fatty acids or their derivatives, is subjected to an acylation reaction.

It also relates to the products obtained according to this said process and to their use in formulations containing foaming agents.

11 Claims, No Drawings

PROCESS FOR THE PREPARATION OF PURIFIED FATTY ALKYLDIETHANOLAMIDES PRODUCTS OBTAINED ACCORDING TO SAID PROCESS AND THEIR USE

Fatty acid alkylethanolamides have been known for many years and employed in formulations for cosmetic use, such as shampoos, foam baths, ..., or for domestic use, such as liquid detergents for washing-up by hand, or for the industry.

Alkylethanolamides have on the formulation a thickening effect which is advantageous as regards the presentation of the product, they also promote a quick development of the foam and increase the stability.

The fatty acid diethanolamides produced according to the conventional methods, contain still a certain quantity of free diethanolamine which, with time and in the presence of nitro-derivatives, are liable to form toxic nitrosamines. Consequently, the European organizations, such as for example Colipa, have recommended, particularly in the field of cosmetics and hygiene, that the content in free diethanolamine of said products be limited to less than 1%.

The fatty acid alkyldiethanolamides are normally prepared by reacting fatty acids or their derivatives, methyl esters or acids chlorides, with diethanolamine.

Their formula is:

$$R-CO-N\begin{array}{c}CH_2-CH_2OH\\ CH_2-CH_2OH\end{array}$$

in which

R is a fatty radical containing between 8 and 22 carbon atoms.

The most conventional amides are obtained with:
natural fatty acids of copra or African oil palm;
fatty acids of tallow or palm;
fatty acids distilled in the form of various fractions, such as: $C_{12}$, $C_{12}-C_{14}$, $C_{12}-C_{16}/C_{16}-C_{18}$ ...;
oleic and oleo-cetylic acids and ricinoleic and undecylenic acids;
synthetic acids;
and more generally, all the natural or synthetic fatty acids normally used in the surface agents industry.

The synthesis of alkyldiethanolamides, from fatty acids or triglycerides, gives products with a high content of free diethanolamide, and in general, these products are currently prepared from the methyl esters of fatty acids, this permitting a reduction of the free diethanolamine content.

In the case of a copra alkyldiethanolamide, the product obtained from methyl esters of copra has the following characteristics:
amide content: higher than 89%
free diethanolamine: 3 to 5%
pH in 10% solution: 9 to 11
aspect: cloudy liquid, heterogeneous at normal temperature.

Said copra diethanolamide is used:
as foam stabilizing agent in shampoos, foam baths and various cleaning or detergent preparations containing anionic or amphoteric surface-active products;
to increase the viscosity of preparations based on anionic surface-active agents, and in particular of alkyl-sulphates.

The Applicant has found that a fatty alkyldiethanolamide, improved as regards its diethanolamine content, its aspect and its irritating action on the mucous membranes, could be obtained by acylating the free amine.

Such acylation can be obtained by using the conventional acylating derivatives, such as anhydrides or acids chlorides, preference being given to acetylation and to the use of acetic anhydride as acetylating agent, for reasons of cost and reactivity.

Acylation tests conducted with:
ethyl acetate
methyl esters of fatty acids
hexamethylene diisocyanate
have revealed an inadequate fixation of the free amine or a product which, having insufficient stability, allowed the free diethanolamine to reappear through ageing.

A copra diethanolamide, prepared by reacting methyl esters, total fatty acids of copra and diethanolamine, has a free diethanolamine content of between 3 and 5%.

Said amide, which is treated with acetic anhydride in order to acetylate the free amine, and then either subjected to a treatment in vacuo, or washed and then dried to eliminate the acetic acid which has formed, leads to a copra diethanolamide whose free amine content is under 1% and whose pH, in dispersion in water at 10%, is between 6 and 8.

Said diethanolamide was found to have unexpectedly improved properties.

From the point of view of ocular tolerance, measured on an unwashed rabbit's eye, according to the French protocol, the improvement was found to be most significant. The index went from 51.7 for the non-treated diethanolamide to 21 for the diethanolamide treated with acetic anhydride.

Such improvement of the ocular tolerance is not linked to a lesser alkalinity of the product; a solution of diethanolamine of pH 10 has an ocular irritation test of 2, therefore it is not irritant for the eye, the irritation tests being conducted at the same pH.

From the point of view of presentation, copra diethanolamide is, after acetylation, a homogeneous limpid liquid at normal temperature whereas the non-acetylated product contains a large part of dense product giving it a heterogeneous and cloudy aspect.

EXAMPLE 1

1,000 kg of diethanolamide from the total fatty acids of copra are prepared by reacting:
390 kg of diethanolamine
720 kg of copra total fatty acids methyl esters
with 17 kg of sodium methylate in solution at 30% in methyl alcohol.

The whole mixture being kept at 80° C. in vacuo.

The temperature is kept up for 5 to 6 hours and the methanol, produced by the reaction, is distilled continuously.

The resulting amide has a free diethanolamine content of about 5%. Said amide is cooled to 40°–45° C., then under a vacuum of 300–400 torr, 50 kg of acetic anhydride are introduced gradually under stirring. The introduction lasts about one hour. The reaction being exothermal, the temperature is kept to 40°–45° C. with, if necessary, a slight cooling down.

Keep for one hour in vacuo at 40°–45° C.

Check that the free amine content is equal to or below 0.15%, if not add a small quantity of acetic anhydride.

Then place in a 50 mm vacuum and bring the temperature to 90°–92° C. under stirring. When the amide has reached that temperature, initiate entrainment and keep it up as long as the acid index is higher than 5.

The resulting amide is a clear liquid; the free diethanolamine content is about 0.5%.

EXAMPLE 2

The same reaction sequence is applied to a diethanolamide of African oil palm topped fatty acids.

The substances used for producing 1,000 kg of said amide are:

diethanolamine: 340.9 kg
African oil palm $C_{12}$–$C_{18}$ methyl esters: 750.0 kg
sodium methylate at 30%: 22.7 kg The remaining operations, being conducted exactly as in Example 1, give an amine in the form of a clear liquid with a free amine content of about 0.5%.

After heating at 40° C. for two weeks, the free amine content remains unchanged.

EXAMPLE 3

An oleic diethanolamide is prepared according to the same reaction sequence, the raw materials used for producing 1,000 kg of this amine being:

diethanolamine: 288 kg
methyl oleate: 769 kg
olein: 8 kg
sodium methylate at 30%: 24 kg The resulting amide has a free amine content less than 1%. Such low content is obtained after washing with water and drying in vacuo of the reaction product.

What is claimed is:

1. A process for the preparation of a fatty acid diethanolamide having a diethanolamine content of less than 1%, comprising the steps of:
   a) reacting diethanolamine with a fatty acid or derivative thereof to produce a raw product containing a fatty acid diethanolamide and at least 1% diethanolamine; and
   b) mixing and reacting with said raw product an acylating agent under conditions sufficient to yield a fatty acid diethanolamide product with a diethanolamine content of less than 1%.

2. Process according to claim 1, wherein the acylating agent is acetic anhydride.

3. Process according to claim 2, wherein the reaction with said acylating agent takes place at 40°–45° C. under a pressure of about 300–400 torr.

4. Process according to claim 1, wherein the raw product has a diethanolamine content of about 3–5%.

5. Process according to claim 1, wherein said fatty acid or derivative thereof is derived from natural fatty acids of copra or African oil palm, tallow, palm, or a mixture thereof.

6. Process according to claim 1, wherein said fatty acid or derivative thereof is oleic acid, oleo-cetylic acid, ricinoleic acid, undecylenic acid, or a mixture thereof.

7. Process according to claim 1, wherein said derivative is a triglyceride, methyl ester, or acid chloride.

8. Process according to claim 1, additionally comprising heating said fatty acid diethanolamide product to about 90° C. under vacuum.

9. A fatty acid diethanolamide having a diethanolamine content of less than 1%, prepared by the process of claim 1 or 2.

10. A formulation comprising an anionic or amphoteric foaming agent and a fatty acid diethanolamide, said fatty acid diethanolamide produced by a process comprising:
    a) reacting diethanolamine with a fatty acid or derivative thereof to produce a raw product containing a fatty acid diethanolamide and at least 1% diethanolamine; and
    b) mixing and reacting with said raw product an acylating agent under conditions sufficient to yield a fatty acid diethanolamide product with a diethanolamine content of less than 1%.

11. Formulation according to claim 1, wherein the acylating agent is acetic anhydride.

* * * * *